United States Patent [19]

Kimble et al.

[11] Patent Number: 4,619,760

[45] Date of Patent: Oct. 28, 1986

[54] ORE FLOTATION AGENT FROM 2-MERCAPTOBENZIMIDAZOLE AND FLOTATION PROCESSES THEREWITH

[75] Inventors: Kenneth B. Kimble; Clarence R. Bresson; Harold W. Mark, all of Bartlesville, Okla.

[73] Assignee: Phillips Petroleum Company, Bartlesville, Okla.

[21] Appl. No.: 729,770

[22] Filed: May 2, 1985

[51] Int. Cl.[4] ........................... B03D 1/14; C09K 3/00
[52] U.S. Cl. ....................................... 209/166; 252/61; 260/455 B; 548/329; 558/247; 558/243
[58] Field of Search ........................... 209/166; 252/61; 260/455 B; 548/329

[56] References Cited

U.S. PATENT DOCUMENTS

| | | | |
|---|---|---|---|
| 1,801,319 | 4/1931 | Moses et al. | 209/166 |
| 2,644,580 | 7/1953 | Robbins, Jr. et al. | 209/166 |
| 3,068,239 | 12/1962 | Miller | 548/329 |
| 3,361,752 | 1/1968 | D'Amico | 548/329 |
| 4,022,686 | 5/1977 | Arakatsu et al. | 209/166 |
| 4,341,715 | 7/1982 | Parlman et al. | 260/455 B |

*Primary Examiner*—Paul Lieberman
*Assistant Examiner*—Robert A. Wax
*Attorney, Agent, or Firm*—Stephen E. Reiter

[57] ABSTRACT

Process for the preparation of ore flotation collectors is disclosed comprising reacting an alkali metal salt of a 2-mercaptobenzimidazole with carbon disulfide. Also disclosed is process for recovery of minerals by flotation employing the novel ore flotation collectors prepared as described above.

13 Claims, No Drawings

ORE FLOTATION AGENT FROM 2-MERCAPTOBENZIMIDAZOLE AND FLOTATION PROCESSES THEREWITH

This invention relates to novel chemical compositions. In one aspect, the invention relates to methods for producing such compositions. In another aspect, the present invention relates to the recovery of minerals by ore flotation employing these novel compositions.

BACKGROUND

Froth flotation is a process for recovering and concentrating minerals from ores. In a froth flotation process, the ore is crushed and wet ground to obtain a pulp. Additives such as mineral flotation or collecting agents, frothing agents, depressants, stabilizers, etc., are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and separated. The froth product or the reject product or both can then be further processed to obtain the desired minerals. Typical mineral flotation collectors include xanthates, amines, alkyl sulfates, arenes, sulfonates, dithiocarbamates, dithiophosphates, fuel oils, and thiols.

It is a continuing goal in the ore-processing industry to increase the productivity of ore flotation processes and, above all, to provide specific procedures which are selective to one ore or metal over other ores or metals present in the treated material. For example, since iron and lead are among the most readily floated metals, it is frequently difficult to obtain selective recovery of one in the presence of significant quantities of the other.

OBJECTS OF THE INVENTION

An object of the invention, therefore, is a selective ore flotation process. Another object of the invention is novel ore flotation chemicals which promote the selective flotation of one or more minerals from a mineral containing solid material.

These and other objects of the invention will become apparent from the disclosure and claims provided herein.

STATEMENT OF THE INVENTION

In accordance with the present invention, we have discovered that the condensation product of an alkali metal salt of a 2-mercaptobenzimidazole and carbon disulfide is a selective ore flotation reagent.

DETAILED DESCRIPTION OF THE INVENTION

In accordance with the present invention, process for the preparation of nitrogen- and sulfur-containing aromatic ore flotation collectors is provided which comprises reacting an alkali metal hydroxide with a 2-mercaptobenzimidazole to give an alkali metal 2-mercaptobenzimidazole salt, thereafter reacting the benzimidazole salt with carbon disulfide under conditions suitable to form a nitrogen- and sulfur-containing aromatic ore flotation collector and finally recovering the solid reaction mass as the product of the condensation process.

In accordance with another embodiment of the invention, novel compositions prepared in accordance with the above described process are provided.

In accordance with yet another embodiment of the present invention, process for the recovery of minerals from solid materials containing such minerals is provided. The recovery process comprises mixing the solid material with water and the inventive collector composition prepared as described above to establish a pulp, aerating the pulp to produce a mineral-bearing froth comprising a first portion of minerals while a second portion of the minerals remain in the pulp fraction, and thereafter recovering the first portion of minerals from the froth.

The synthetic process of the present invention first involves the reaction of an alkali metal hydroxide, i.e., potassium hydroxide, sodium hydroxide, or lithium hydroxide, with a 3-mercaptobenzimidazole having the structure:

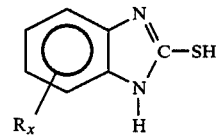

wherein R is a $C_1$–$C_6$ carbon radical and x is 0–4, inclusive. Suitable reaction conditions for this neutralization reaction can be readily determined by those of skill in the art. It is preferred that the admixture of reagents be carried out at a controlled rate such that excessive reaction temperatures are avoided.

The alkali metal salt of 2-mercaptobenzimidazole is then reacted with a roughly equimolar amount of carbon disulfide, then warmed to about reflux temperature (in the range of about 30°–60°C.) for about 0.5–6 hours. After this time period the reaction mixture is allowed to cool and stand at room temperature for several hours (4–24 hours), before collecting the crystalline product by suitable techniques, such as for example, filtration, decantation, or the like. The products so recovered are useful for example, in ore flotation processes.

A further embodiment of this invention resides in an ore flotation process. More specifically, such further embodiment of this invention resides in a process for separating valuable ore materials from gangue materials. The ore flotation process of this invention distinguishes over the known ore flotation processes primarily in the employment of a new flotation agent. The recovery process involves crushing of the ore and ore grinding to obtain a pulp. The flotation agent is incorporated in the pulp which is then aerated to produce a froth at the surface which is rich in valuable ore materials but depleted of the gangue materials or vice versa. The ore materials, optionally, after additional flotation and frothing steps, are recovered. Frothing agents, selective depressants and stabilizers which are well known in the art can be used in the various steps.

The flotation agent employed in the practice of the present invention is the nitrogen- and sulfur-containing aromatic ore flotation collector prepared as described above. Examples of such compounds useful as collectors in the practice of this invention are those prepared from such 2-mercaptobenzimidazoles as 2-mercaptobenzimidazole, 2-mercapto-4-methylbenzimidazole, 2-mercapto-5-methylbenzimidazole, 2-mercapto-4- ethylbenzimidazole, 2-mercapto-5-ethylbenzimidazole, and the like.

The amount of nitrogen- and sulfur-containing aromatic ore flotation collector employed in the process of this invention is not critical. The quantity will depend upon whether it is being used with an ore or a concentrate and whether there is a large or small amount of mineral to be collected. Generally, the amount of nitrogen- and sulfur-containing aromatic ore flotation collector employed in the process of the present invention will be in the range of from about 0.001 lb to 1.0 lbs of the inventive collector per ton of solids (lbs/ton). Preferably the inventive ore flotation collector will be used in a quantity in the range from about 0.01 to about 0.5 lbs/ton of solids.

It is generally believed that the nitrogen- and sulfur-containing aromatic ore flotation collectors disclosed herein are useful for the selective flotation of certain metal sulfide minerals during one flotation processes. It is also understood that the nitrogen- and sulfur-containing aromatic ore flotation collectors may selectively collect a mixture of metals or minerals that are contained in a particular mining deposit or ore, said mixture being further separated by subsequent froth flotations or any other conventional separating methods. The nitrogen- and sulfur-containing aromatic ore flotation collectors herein disclosed are particularly useful for flotation of minerals based on copper, nickel, iron, lead, gold and zinc from the total ore. Examples of such minerals include, but are not limited to, such materials as

| Copper-bearing ores: | |
|---|---|
| Covellite | CuS |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_{12}Sb_4S_{13}$ |
| Tennanite | $Cu_{12}As_4S_{13}$ |
| Cuprite | $Cu_2O$ |
| Tenorite | CuO |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Lead-bearing ore: | |
| Galena | PbS |
| Zinc-bearing ores: | |
| Sphalerite | ZnS |
| Zincite | ZnO |
| Smithsonite | $ZnCO_3$ |
| Iron-bearing ores: | |
| Pyrite | $FeS_2$ |
| Marcasite | $FeS_2$ |
| Pyrrhotite | $Fe_7S_8$ |
| Daubreelite | $FeSCrS_3$ |
| Nickel-bearing ores: | |
| Pentlandite | (FeNi)S |
| Millerite | NiS |
| Niccolite | NiAs |
| Gold-bearing ores: | |
| Sylvanite | $(AgAu)Te_2$ |
| Calaverite | $AuTe_2$ |

The presently preferred ores in connection with which the process of this invention is applied are copper, zinc, lead and iron ores or minerals.

SEPARATION CONDITIONS

Any froth flotation apparatus can be used in this invention. The most commonly used commerical flotation machines are the Agitar (Galigher Co.), Denver Sub-A (Denver Equipment co. ), and the Fagergren (Western Machinery Co.). Smaller laboratory scale apparatus such as the hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of a mercaptobenzimidazole-carbon disulfide condensation product useful as a mineral sulfide collector in an ore flotation process. To a 500 milliliter round bottom flask fitted with a stirrer, thermometer and dropping funnel was added 118 milliliters of water and 14.0 grams (0.35 mole) of sodium hydroxide. After the sodium hydroxide had completely dissolved and the temperature cooled below about 40° C., 50 grams (0.33 mole) of 2-mercaptobenzimidazole was slowly added with no exotherm. To this stirred mixture was then added 25.4 grams (0.33 mole) of carbon disulfide. The mixture was gently refluxed for 2 hours and then allowed to stand at ambient room temperature overnight. The crystalline material that formed was filtered and dried in a vacuum oven (100° C.). The product was subjected to elemental analysis, the result of which suggested this product was not the expected sodium 2-benzimidazolyl trithiocarbonate.

| | % C | % H | % N | % S | % Na |
|---|---|---|---|---|---|
| Calculated for $C_8H_5N_2NaS_3$ | 38.69 | 2.03 | 11.28 | 38.78 | 9.26 |
| Found | 53.11 | 4.05 | — | 20.37 | — |

EXAMPLE II

This example describes the procedure used to evaluate the condensation product prepared in Example I. To a grinding mill was added 1000 grams of a Pb/Zn-containing ore (Cyprus Anvil Mine, Yukon, Canada) along with 300 milliliters of water and 0.016 lb/ton ore of a 1 weight percent aqueous solution of sodium ispropyl xanthate. The mixture was ground for 25 minutes after which it was transferred to a 2.5 liter capacity Denver flotation cell along with enough water such that the surface of the slurry was within about 1 to 2 inches from the top lip of the cell. After a short conditioning time (1 minute) at 1200 rpm, the mixture was floated for 3 minutes to primarily remove Pb. To the cell was then added 0.02 lb/ton ore of aqueous sodium isopropyl xanthate and the mixture floated for 4 minutes. This second float was referred to as the first Pb scavenger float. A second Pb scavenger float was similarly carried out using 0.02 lb/ton ore of aqueous sodium isopropyl xanthate. The first Pb concentrate and the two combined scavenger floats were filtered, dried and analyzed. To the flotation cell was then added 1.2 lbs/ton ore of a 10 weight percent aqueous $CuSO_4$ as a zinc activator followed by 0.07 lb/ton ore of more aqueous sodium isopropyl xanthate.

After conditioning for 2 minutes the slurry was floated for 3 minutes to collect a Zn rougher concentrate. Two Zn scavenger floats were conducted for 4 minutes each using 0.04 lb/ton ore of aqueous sodium isopropyl xanthate in each float. Again the floats were filtered, dried and analyzed. A duplicate flotation run was made and the calculated weight percent recoveries of Pb/Zn and Fe averaged. Table I shows the results from this flotation series (Run 1) as well as results from other runs using control runs (Nos. 2, 3) and the inventive runs (No. 4).

TABLE I

Comparison of Ore Flotation Collectors
(1000 grams Cyprus Anvil Ore)
2.5% Pb, 2.51% Zn, 18.55% Fe

| Run No | Collector | Dosage lb/ton[a] | Average Wt % Recovery Pb | Zn | Fe |
|---|---|---|---|---|---|
| 1 (a) Grind | NaIPX[b] | 0.16 | | | |
| (b) Pb float | NaIPX | 0.04 | 86.3 | 47.6 | 23.2 |
| (c) Zn float | NaIPX | 0.15 | | | |
| | CuSO$_4$ | 1.2 | 5.8 | 51.1 | 27.4 |
| | Total | | 92.1 | 98.7 | 50.6 |
| 2 (a) Grind | NaIPX | 0.12 | | | |
| (b) Pb float | NaIPX | 0.08 | 90.0 | 60.6 | 49.8 |
| (c) Zn float | NaIPX | 0.15 | | | |
| | CuSO$_4$ | 1.2 | 3.8 | 38.1 | 8.3 |
| | Total | | 93.8 | 98.7 | 58.1 |
| 3 (a) Grind | ABTTC[c] | 0.06 | | | |
| (b) Pb float | ABTTC | 0.08 | 58.2 | 17.6 | 8.3 |
| (c) Zn float | NaIPX | 0.15 | | | |
| | CuSO$_4$ | 1.2 | 29.6 | 80.3 | 31.3 |
| | Total | | 87.8 | 97.9 | 39.6 |
| 4 (a) Grind | MBCD[d] | 0.12 | | | |
| (b) Pb float | MBCD | 0.08 | 78.5 | 33.4 | 13.8 |
| (c) Zn float | NaIPX | 0.15 | | | |
| | CuSO$_4$ | 1.2 | 13.7 | 64.9 | 18.2 |
| | Total | | 92.2 | 98.3 | 32.0 |

[a]Dosage values represent totals after 3 floats (rough plus 2 scavenger floates).
[b]Sodium isopropyl xanthate.
[c]Allyl butyl trithiocarbonate.
[d]Invention mercaptobenzimidazole-carbon disulfide condensation product.

These results show that the inventive collector gives a Pb and Zn recovery comparable to the controls using sodium isopropyl xanthate but the amount of Fe recovered is significantly less which indicated that the purity or grade, particularly of the Pb is greatly enhanced. Similarly the grade or purity of Zn in the combined Zn floats is significantly better using the inventive collector than the two xanthate controls. The data also indicates the inventive collector gives a higher weight percent recovery of Pb and Zn along with a better grade of each than when a similar collector, allyl butyl trithiocarbonate, was used (Run No. 3).

The examples have been provided merely to illustrate the practice of our invention and should not be read as to limit the scope of our invention in any way. Reasonable variations and modifications, not departing from the essence and spirit of our invention, are contemplated to be within the scope of patent protection and sought.

We claim:

1. A process for producing a nitrogen- and sulfur-containing aromatic ore flotation collector which comprises:
   (a) reacting an alkali metal hydroxide with a 2-mercaptobenzimidazole having the formula:

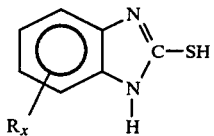

wherein R is a $C_1$–$C_6$ carbon radical and x is 0–4, inclusive, then thereafter
   (b) reacting the production of (a) with carbon disulfide under conditions suitable to form said nitrogen and sulfur-containing aromatic ore flotation collector, and
   (c) recovering the solid reaction mass produced in (b) as the product of the process.

2. A process in accordance with claim 1 wherein said 2-mercaptobenzimidazole is 2-mercaptobenzimidazole.

3. A process in accordance with claim 1 wherein said alkali metal hydroxide is sodium hydroxide.

4. A process in accordance with claim 1 wherein said conditions suitable to form said nitrogen- and sulfur-containing aromatic ore flotation collector comprise a temperature in the range of about 30°–60° C. for a time in the range of about 0.5–6 hours.

5. The composition produced by the process of claim 1.

6. The composition produced by the process of claim 2.

7. The composition produced by the process of claim 3.

8. The composition produced by the process of claim 4.

9. A process for recovering minerals from solids containing said minerals which comprises:
   (a) mixing said solids with water and a collector produced by the process of claim 1 to establish a pulp;
   (b) aerating said pulp to produce a mineral-bearing froth containing a first portion of said minerals and a second portion of gangue minerals in said pulp; and
   (c) recovering said first portion of said minerals from said mineral-bearing froth.

10. A process for recovering minerals from solids containing said minerals which comprises:
    (a) mixing said solids with water and the collector produced by the process of claim 2 to establish a pulp;
    (b) aerating said pulp to produce a mineral-bearing froth containing a first portion of said minerals and a second portion of gangue minerals in said pulp; and
    (c) recovering said first portion of said minerals from said mineral-bearing froth.

11. A process for recovering minerals from solids containing said minerals which comprises:
    (a) mixing said solids with water and a collector produced by the process of claim 3 to establish a pulp;
    (b) aerating said pulp to produce a mineral-bearing froth containing a first portion of said minerals and a second portion of gangue minerals in said pulp; and
    (c) recovering said first portion of said minerals from said mineral-bearing froth.

12. A process for recovering minerals from solids containing said minerals which comprises:
    (a) mixing said solids with water and a collector produced by the process of claim 4 to establish a pulp;

(b) aerating said pulp to produce a mineral-bearing froth containing a first portion of said minerals and a second portion of gangue minerals in said pulp; and
(c) recovering said first portion of said minerals from said mineral-bearing froth.

13. A process for recovering minerals from ore which comprises (a) mixing crushed ore containing said minerals with water and a collector produced by the process of claim 1 to establish a pulp;
(b) aerating said pulp to produce a mineral-bearing froth containing a first portion of said minerals and a second portion of said minerals in said pulp; and
(c) recovering said first portion of said minerals from said mineral-bearing froth.

* * * * *